United States Patent [19] [11] 4,427,779
Reckel et al. [45] Jan. 24, 1984

[54] AGGLUTINATION-INHIBITION TEST METHOD FOR DETECTING IMMUNE COMPLEXES

[75] Inventors: Rudolph P. Reckel, Bridgewater; Joanne L. Harris, Annandale, both of N.J.

[73] Assignee: Ortho Diagnostic Systems Inc., Raritan, N.J.

[21] Appl. No.: 382,262

[22] Filed: May 26, 1982

[51] Int. Cl.$^3$ .................................................. G01N 33/54
[52] U.S. Cl. .................................... 436/507; 436/519; 436/520; 436/821
[58] Field of Search .................. 422/61; 436/506, 507, 436/509, 520, 521

[56] References Cited

U.S. PATENT DOCUMENTS

| | | | |
|---|---|---|---|
| 3,873,684 | 3/1975 | Fujita | 436/521 X |
| 4,062,935 | 12/1977 | Masson et al. | 424/12 |
| 4,138,213 | 2/1979 | Masson et al. | 23/230 B |
| 4,141,965 | 2/1979 | Soothill et al. | 424/12 |
| 4,143,124 | 3/1979 | Masson | 436/509 |
| 4,210,622 | 7/1980 | Soothill et al. | 422/61 |

OTHER PUBLICATIONS

Zubler, R. H. et al., The $^{125}$I-Clq Binding Test For The Detection of Soluble Immune Complexes, In Vitro Methods In Cell-Mediated and Tumor Immunity, by Bloom & David, pp. 565-572, 1976 Acad. Press.
Lachmann, P. J., Studies with Monoclonal Antibodies to Complement Components, Immunology Today, 144, Aug. 1981.
Hautanen, A. et al., C3c-Binding ELISA For The Detection of Immunocoglutinins and Immunoglobulin Aggregates, Methods In Enzymology, vol. 74:39-58-8-591 (1981).
Pribor, H. C. et al., Circulating Immune Complexes, Clinical Forum, pp. 23-25, May 1979.
Hay, F. C. et al., Routine Assay For The Detection of Immune Complexes of Known Immunoglobulin Class Using Solid Phase Clq. Clin. Exp. Immunol., 24,396-400 (1976).
Nydegger, U. E. et al., Circulating Immune Complexes in the Serum in Systemic Lupus Erythematosus and in Carriers of Hepatitis B Antigen, J. Clin. Invest., 54:297-309, Aug. 1974.
Rossen, R. D. et al., Detection of Immune Complex--like Materials in Cancer Patient's Sera: A Comparative Study of Results Obtaining With a Clq Deviation and Clq Binding Tests, J. Lab Clin. Med., 191-204, Feb. 1978.
Rosen, R. D. et al., Blockade of the Humoral Immune Response: Immune Complexes In Cancer, Chapter 8, Cancer Immunology: vol. 7, Harold Waters, Garland Publication, 1980.
Theofilopoulos, A. N., The Raji, Conglutinin, and Anti--C3 Assays for the Detection of Complement-Fixing Immune Complexes, Methods in Enzymology, vol. 74:511-531, 1981.
Siersted, H. C. et al., Quantitation of Circulating Immune Complexes by Combined PEG Precipitation and Immunoglobulin Specific Radioimmunossay, Methods in Enzymology, vol. 74:538-543, 1981.
Glikmann, G. et al., Detection and Quantitation of Circulating Immune Complexes by the Clq-Protein A Binding Assay, Methods in Enzymology, vol. 74:571-587, 1981.
Virella, G. et al., Isolation of Soluble Immune Complexes from Human Serum: Combined Use of Polyethylene Glycol Precipitation, Gel Filtration, and Affinity Chromatography on Protein A-Sepharose, Methods In Enzymology, vol. 74:644-663, 1981.
Mayer, M. M., The Complement System, Chapter 14, Immunology, edited by Burnet, W. H. Freeman and Company, 1976.
Theofilopoulos, A. N. et al., The Biology and Detection of Immune Complexes, Advances in Immunology, 28:89, 1977.
Zubler, R. H. et al., Immune complexes in Clinical Investigation, Recent Advances in Clinical Immunology, Thompson R. A.-Editor Churchill Livingstone, New York, p. 125, 1977.
Carpentier, N. A. et al., Clinical Relevance of Circulating Immune Complexes in Human Leukemia, J. Clin. Invest., 60:874, 1977.
Poulton, T. A. et al., Immune Complexes in Ovarian Cancer, The Lancet, p. 72-73, 1978.
Luthra, H. S. et al., Immune Complexes in Sera and Synovial fluids of Patients with Rheumatoid Arthritis, J. Clin. Invest., 56:458, 1975.
Grigor, R. et al., Systemic Lupus Erythematosus, Annals of the Rheumatic Diseases, 37:121-128, 1978.
Levinsky, J. et al., Serum Immune Complexes and Disease Activity In Lupus Nephritis, The Lancet, p. 564, Mar. 12, 1977.
Theofilopoulos, A. N. et al., Detection of Immune Complexes: Techniques and Implications, Hospital Practice, p. 107, May 1980.
Horowitz, B. et al., Development of Hemagglutination Assays, Vox Sang, 33:324-334, 1977.
Yonemasu, K. et al., Clq: Rapid Purification Method For Preparation of Monospecific Antisera and for Biochemical Studies, The Journal of Immunology, 106, 2:304-313, 1971.
Gabriel, A. et al., Detection of Immune Complexes, Journal of Clin. Invest., 59:990-1001, May 1977.
Heusser, C. et al., Effect of Chemical and Enzymatic Radioiodination on In Vitro Human Clq Activities, Journal of Immunology, vol. 110, 3:820-828, Mar. 1973.

Primary Examiner—Sidney Marantz
Attorney, Agent, or Firm—Mark A. Hofer

[57] ABSTRACT

Method for detecting circulating immune complexes containing endogenously bound Clq. Capillary tubes are filled with a mixture of Clq coated GPO reagent cells, rabbit anti-Clq antibodies, and precipitate from the biological fluid sample containing immune complexes. The mixture is allowed to react and the tubes read for the presence or absence of agglutination indicative of the absence or presence of said immune complexes respectively.

7 Claims, No Drawings

AGGLUTINATION-INHIBITION TEST METHOD FOR DETECTING IMMUNE COMPLEXES

FIELD OF THE INVENTION

This invention relates to the analysis of biological fluids for the presence of immune complexes, specifically circulating immune complexes containing endogenously bound Clq.

BACKGROUND OF THE INVENTION

Immune complexes may be found in plasma, serum, other body fluids as well as in tissues at site of putative immune complex deposition. The methods presently available for detection of immune complexes at these various locations are different and often limited to those site. The invention described herein is exceptionally suitable for the detection of immune complexes found in plasma, serum or other body fluids.

The formation of immune complexes generally results from the interaction of antibodies with antigens and although in most instances, the formation of an immune complex does not lead to evident disease, it often serves a physiological role in homeostasis. See for instance, Theofilopoulos A. N., et al., The Biology and Detection of Immune Complexes, Adv. Immunol. 28:89, 1977. It is, however, important to note that the greatest concentration of immune complexes can be found in patients with infections and autoimmune diseases. Although the comprehension of human immune complex diseases has seen a tremendous expansion within the last twenty years it is to be noted that there is still much physiologic activity related to immune complex formation and resultant effects that requires further clarification, understanding and explanation. To date, the presence of immune complexes has been associated with infections from bacteria, viruses, parasites, different malignancies and with acute and chronic nephritis accompanying serum sickness generally associated with the deposition of immunie complex onto tissue. Such human immune complex diseases are often characterized by arthritis and nephritis and may be variably accompanied by leucopenia, agranulocytosis and thrombocytopenia. Further, it has been noted that deposition of immune complexes on blood vessel walls often leads to infiltration of the deposition site by inflammatory cells resulting in the consequential functional impairment of the inflamed organ structure. See for instance: Zubler R., Lambert P., Immune Complexes in Clinical Investigation, Recent Advances in Clinical Immunology, Thompson R. A. (Ed) Churchill Livingstone, NY, p. 125, 1977; Carpentier N. A., et al., Clinical Relevance of Circulating Immune Complexes in Human Leukemia, J. Clin. Invest., 60:874, 1977; and Poulton T. A. et al., Immune Complexes in Ovarian Cancer, Lancet 1978.

The term "generalized immune complex disease" has often been used to connote the deposition of circulating immune complexes throughout the body especially likely to occur where conducive factors are present. Typically these include small vessels and slow circulation therethrough. Other considerations such as genetic and host related factors as well as variable tissue affinities influence the rate and extent to which disease systems are produced.

Still other diseases that have been implicated include systemic lupus erythematosus, inflammatory diseases of the bowels generally chronic in nature, glomerulonephritis, and rheumatoid arthritis. See Luthra H. S., et al., Immune Complexes in Sera and Synovial Fluids of Patients with Rheumatoid Arthritis, J. Clin. Invest. 56:458, 1975; and Grigor R., SLE: A Prospective Analysis, Ann. Rheum. Dis. 37:121, 1976; Levinsky R. J., et al., Serum Immune Compexes and Disease Activity in Lupus Nephritis, Lancet 1:564, 1977. The profound local and systemic effects caused by immune complex aggregates in circulation and subsequent deposition as well as their effects on cell mediated immune responses highlights the desirability of detecting circulating immune complexes in the clinical environment. A summary and listing of relevant references concerning the effects of immune complexes has been reported in "The Role of Immune Complexes In Disease," WHO Scientific Group, Geneva 1977, ISBN 92 4 120606 3.

Conventionally, immune complexes have been detected by two generic groups of methods, namely the physical-chemical methods which evaluate particular characteristics of the complex size, charge and temperature dependent solubility while the biological assay methods are generally based on immune complex effects on receptor systems such as blood cells and platelets, or on soluble protein such as complement-N-rheumatoid factor. Of these two groups, it is the latter in which this invention may be most appropriately classified.

Biological methods directed against humoral receptors include inactivation of $CH_{50}$ units in reference serum, inhibition of $^{125}I$-Clq binding, insolubility of reaction product between Clq in complexes, fixation of $^{125}I$-Clq to the Fc fragments of complexed Ig, binding of Fc in complexes to insolubilized Clq, fixation of RhF and Clq to the Fc portion of complexed antibodies, and affinity of conglutinin for complex bound C3. Methods directed against cellular receptors include interaction with platelet Fc receptors as well as interaction with C3b receptors on a lymphoblastoid cell line such as a Raji cell. These methods have been generally referenced and described in Nydeggar V. E., Soluble Immune Complexes In Human Disease, CRC Critical Review in Clinical Laboratory Science, July 1980, pages 123-170; Theofilopoulos A. N. et al., Detection of Immune Complexes: Techniques and Implications, Hospital Practice, May 1980; and Zubler R. , et al., Detection of Immune Complexes in Unheated Sera by a Modified I-Clq Binding Test, J. Immunol. 116(1):232, 1976.

The foregoing list, although representative, is still not comprehensive as additional methods have been described and compared for effectiveness in specific disease conditions in "A WHO Collaborative Study For the Evaluation of 18 Methods For Detecting Immune Complexes And Serum" by Lambert et al., J. Clin. Lab. Immuno. 1:1-15, 1978.

Included in that report are five methods directed towards the detection of Clq, a complement protein. One method relies on the principle that Clq acts as a receptor for aggregates containing either IgG or IgM, and further involving rheumatoid factor dependent on the affinity of IgMrf for aggregates of IgG or IgA. Another method is directed to conglutinin binding which is, in turn, dependent upon a Ca++ dependent interaction of bovine conglutinin with immune complex bound C3b that has been cleaved by a C3b inactivator. Also included are methods directed against receptors of C3b or C3d with complement coated immune complexes operative in Raji cell radioimmune type assays;

C3b or C3d lymphocyte rosette formation inhibition tests; and the interaction of immune complexes with the Fc portion of immunoglobulins in the formats of: platelet aggregation, macrophage uptake inhibition, K cell cytotoxicity inhibition, and neutrophil inhibition tests.

These methods and tests for the detection of immune complexes have traditionally suffered from their overall complexity and their extensive, critical reagent requirements. It is an object of the present invention to provide a greatly simplified procedure especially useful in clinical environments where efficiency and throughput or turnover time are of paramount importance.

A test involving rheumatoid factor and Clq for the analysis of antigen antibody complexes has been described in U.S. Pat. No. 4,143,124 to Masson et al. Although this reference is primarily directed towards the detection and analysis of antigen antibody formation, it relies on the fact that such a formation has the ability to combine with rheumatoid factors as well as the Clq component of complement. Entailed in the disclosed test is the insolubilization of rheumatoid factor or Clq onto a solid-phase substrate which is then contacted with a fluid containing the immune complexes to be detected. The reacted and immobilized immune complexes are then freed from the substrate and allowed to react with soluble rheumatoid factor or Clq and particles such as red blood cells coated with immunoglobulins. Agglutination of the particles is interpreted to indicate the absence of antigen-antibody complexes in the original sample. Such a procedure disadvantageously entails procedural steps for freeing the bound antigen-antibody complexes to permit subsequent reaction therewith. Further, the test depends upon the complete lack of cross-reactivity of rheumatoid factor or Clq with free antigen or free antibody in the original sample fluid.

It is an object of the present invention to avoid these disadvantages and to provide a simplified system for immune complex detection.

Another assay procedure for immune complexes is described by Soothill et al. in U.S. Pat. No. 4,141,965. A kit, utilizing the same assay procedure, has been provided in Soothill's U.S. Pat. No. 4,210,622. The procedure taught analyzes immune complexes by detecting a constituent thereof. In order for the system to be effective, the constituent must be able to produce non-human IgM antibodies and, to be attachable to a latex particle. The constituent, after attachment to the latex particle, and after addition to IgM and to the immune complex containing sample, permits detection of immune complexes as indicated by the absence of agglutination of the latex particles.

It is an object of the present invention to provide a system that is not limited to the production of non-human IgM antibodies nor requiring the attachment of such a constituent to a latex particle.

SUMMARY OF THE INVENTION

In accordance with the principles and objectives of the present invention, methods are provided for the detection of immune complexes containing endogenously bound Clq which immune complexes may be freely circulating in a biological fluid. Reagent cells are provided having coated thereon Clq. These cells are added to the isolated immune complex, preferably by precipitation from the biological fluid sample, and to non-human anti-Clq immunoglobulin. A capillary tube is filled with the mixture, and the immunological reaction permitted to occur under appropriate conditions. The capillary tube is then read for the presence or absence of agglutination of the reagent cells thereby indicative of the absence or presence of immune complexes containing endogeneously bound Clq respectively. The capillary tube is preferably sealed and inverted in a manner as set forth below. Ideally, the reagent cell are human group O cells as described hereinafter.

The anti-Clq immunoglobulin may be advantageously obtained from rabbits immunized with purified Clq. Such a procedure provides polyclonal antibodies in sufficient quantities for good sensitivity at a comparatively moderate cost (vis-a-vis monoclonal antibodies), especially desirable in view of the generally escalating costs in the clinical environment. The immune complex may be advantageously isolated from the biological sample fluid by precipitation with an affective amount of polyethylene glycol (PEG). It has also been found advantageous to recline the inverted capillary tube against a cool light source in order to aid in the subsequent determination of agglutination. For instance, it has been found advantageous to employ an angle of approximately 60° although other angles in this neighborhood may also be equally effective.

DETAILED DESCRIPTION OF THE INVENTION AND BEST MODE

Anti-Clq immunoglobulin was obtained from rabbits by immunization using 10 micrograms Clq emulsified in complete Freunds Adjuvant and administered twice through the foot pad. The antisera was harvested four to six weeks after onset of immunization and processed as heat inactivated serum containing 0.02% sodium azide as a preservative. It was found advantageous to use human GPO (group O, and preferably Rh negative in order to present a minimum number of antigens thereby reducing conflicting cross-reactivity with immunoglobulins from the sample) red cells for the reagent cells, however, particles artificially produced (for instance latex particles) are also contemplated.

The Clq coated red cells were prepared by adding between 1.5 and 10 micrograms Clq to 1 ml of 8% double aldehyde treated cells described by Horowitz in The Development of Hemeagglutination Assays, Vox Sang 33:324–334, 1977.

The concentrations of the rabbit anti-Clq reagent and Clq sensitized human GPO red cells were adjusted so that (1) when mixed, the cells would agglutinate in a 50 microliter capillary tube within one hour and (2) complete inhibition of agglutination could be effected by 40 nanograms of Clq. Thus, the following was observed:

| Concentration of Purified Clq Solution in Micrograms/ml | 10 | 6 | 4 | 2 | 1 | 0.5 | 0 |
|---|---|---|---|---|---|---|---|
| Agglutination Reaction | 0 | 0 | 0 | 3 | 3 | 3 | 3 |

Agglutination is defined as a smooth uniform mat of cells which settles to the back of the capillary tube (assuming the tube is inclined, otherwise generally centrally throughout the tube) and occupies most of the diameter of the capillary tube. Inhibition is defined as a smooth narrow line of cells which settles to the back of the capillary tube. Ranges of agglutination are assigned in accordance with usage common in the blood-banking field.

The Clq used for standardizations, and preparations of the red cells and immunization of rabbits had purities of 96% or better and was prepared from fresh serum by the methods described by Yonemasu et al., Clq: Rabbit Purification Method For Preparation of Monospecific Antisera and For Biochemical Studies, J. Immunol. 106:304, 1971.

The isolation of circulating immune complexes (CIC) from human sera was effected by precipitation with polyethylene glycol. The serum may be obtained from whole blood collected and allowed to clot for 1-2 hours at ambient temperature. It is, however, preferred that whole blood clotted at 2°-8° C., defibrinated plasma, specimens collected as anticoagulated plasma and then clotted, or samples containing evidence of bacterial contamination not be used. Centrifugation of the clotted whole blood at an RCF of 1000-1500 g for 10 min. at room temperature permits the separation of serum which may then be removed by any convenient method which is preferably chosen to minimize cellular debris contamination of the serum. Specimens may be stored at 2°-8° C. for 48 hours or −70° C. for 3 months prior to testing, however, heat inactivated serum or serum stored at −20° C. is preferably not used.

To isolate the circulating immune complex from serum, the serum is adjusted to contain 0.1 M ethylenediaminetetraacetic acid (EDTA) by adding 150 microliters 0.13 M EDTA, pH 7.2 to 50 microliters of ambient serum in a polystyrene test tube. The serum is treated with EDTA to prevent non-specific precipitation of complement component Cl. The mixture is incubated for 30 minutes at 37° C. to convert the serum Cl to Clq. Following incubation the test tubes containing the mixture are transferred to a 0°-2° C. crushed ice bath and 1 ml of 3% PEG 6000 (PEG in pH 8.5 borate buffer) is added to bring the final PEG concentration to 2.5%. Ideally, the test tubes employed are made of polystyrene and not glass. After mixing and incubating for 60 minutes in the ice bath, the tubes are centrifuged at 1500 g at 2°-8° C. for twenty minutes. The supernatent is decanted and the inverted tubes blotted on absorbent paper. The remaining precipitate is resuspended with 1 ml of cold 2.5% PEG in pH 8.5 borate buffer to remove excess Clq and again centrifuged as before.

Following the same procedure previously indicated, the supernatent is again removed. The remaining washed precipitate is dissolved in 100 microliters of 0.9% saline.

Procedural Example of the Clq-anti-Clq Agglutination Reaction, Inhibition and Standard Testing for Clq in the isolated circulating immune complex sample with an appropriate standard is advantageously performed by the following procedure:

Adjoining wells of a microtiter plate (from Linbro No. 76-321-05; V. Bottom; Unprocessed Plates or their Equivalent) are labeled as Test and Control for each dissolved precipitate under test. To the Test well is added: 25 microliters rabbit anti-Clq and 10 microliters of dissolved PEG 6000 precipitate or a Clq standard. The anti-Clq sera and precipitate is mixed by tapping the plate to agitate the well contents. Thereafter, 25 microliters of Clq reagent cells are added and mixed similarly. To the Control well are added: 25 microliters antibody diluent and 10 microliters of dissolved PEG 6000 precipitate and mixed by gentle agitation of the well contents. Thereafter, 25 microliters of reagent Clq cells are added and similarly mixed.

Fifty microliter capillary tubes (Clay Adams-Accufill 90, No. 4622) are filled from the contents of the well. Each end of the capillary tube is then sealed with clay (Miniseal TM -Cat. No. B4425-1, Scientific Products, McGraw Park, Ill) or other equivalent substance and placed, sealed end down, on a cool light source ideally positioned at a 60° angle from a level horizontal plane. Such a light source is available from I²R, Chaltenham, Pa. The mixture within the capillary tubes is allowed to settle for 60 minutes at ambient (20°-24° C.) temperature. The capillary tube contents are then examined to determine the presence or absence of agglutination. The absence of agglutination is typically characterized by the diffuse distribution of cells throughout the tube while agglutination may be observed by the presence of a relatively sharply outlined thread running the length of the tube of agglutinated cells.

The reactions and results may be summarized as follows:

I. A sample negative for Clq bound to circulating immune complex (CIC-Clq) will result in agglutination according to the following reaction:

A. Reaction in Test (T) Capillary
Rabbit Anti-Clq
+

| Solubilized PEG → precipitate with no CIC-Clq | Rabbit + Anti-Clq | Stabilized → RBC Coated with Clq | Agglutination |
|---|---|---|---|

B. Reaction in Control (C) Capillary Containing Antibody Diluent
Antibody Diluent
+

| Solubilized PEG → precipitate with no CIC-Clq | Antibody + Diluent | Stabilized → RBC Coated with Clq | No Agglutination |
|---|---|---|---|

II. A sample positive for Clq bound to circulating immune complex (CIC-Clq) will result in an inhibition reaction as follows:

A. Reaction in Test (T) Capillary
Rabbit Anti-Clq
+

| Solubilized → PEG precipitate with CIC-Clq | Neutralized + Rabbit Anti-Clq | Stabilized → RBC Coated with Clq | No Agglutination (i.e., Inhibition) |
|---|---|---|---|

B. Reaction in Control (C) Capillary Containing Antibody Diluent
Antibody Diluent
+

| Solubilized PEG → precipitate with CIC-Clq | Antibody + Diluent | Stabilized → RBC Coated with Clq | No Agglutination |
|---|---|---|---|

Standardization Procedure

Purified heat aggregated human IgG (HAG) may be used to standardize the above described Clq agglutination inhibition test by adding it directly to freshly drawn human serum at a final concentration of 500 micrograms/ml serum. Purified human IgG (160 milligrams/ml) may be obtained in a liquid format from Ortho Diagnostic Systems Inc. (Route 202, Raritan, NJ 08869) and diluted to 25 milligrams/ml with glycine buffered saline at a pH of approximately b 8.2. Heating the human IgG at 60° C. for 10 minutes in a water bath aggregates the IgG to form HAG. 150 milligrams of the HAG may be chromatographed on an ULTROGEL ACA 34 (2.6 cm×100 cm, 250 ml bed volume). The IgG is eluted with glycine buffered saline at a pH of 8.2. Measuring the optical density at approximately 280 nm permits the identification of 3 predominant peaks, peak 1 composed primarily of IgG monomer, peak 2 of dimer; and peak 3 of material greater than trimer and essentially pentameric in composition. The most concentrated protein factions occurring in the third peak are collected and approximately 15 to 20 milligrams of HAG may be obtained with an average combined concentration of 1500 micrograms/ml. As previously indicated, the HAG is then added to the human serum to form a concentration of 500 micrograms/ml serum. Following a 30 minute incubation period at room temperature, the serum is then diluted with fresh serum to give final HAG concentrations of 100, 50, 25 and 10 micrograms/ml.

Utilizing the polyethylene glycol precipitation method previously described permits the isolation of immune complexes from these HAG-sera concentrations. It was found that C1q anti-C1q agglutination reaction can be inhibited by dissolved precipitate from the serum containing 50 micrograms/ml HAG 100% of the time and inhibited by dissolved precipitate from the 25 micrograms/ml HAG serum 50-75% of the time. If it is assumed that there is a 100% recovery of HAG by the test method, then the sensitivity of the test may be placed at 125-250 micrograms HAG. The following table provides the agglutination reactions observed:

TABLE I

|  | Agglutination Reaction |
|---|---|
| 100 micrograms/ml HAG in fresh serum | 0 |
| 50 micrograms/ml HAG in fresh serum | 0 |
| 25 micrograms/ml HAG in fresh serum | 0 |
| 10 micrograms/ml HAG in fresh serum | 3 |
| Fresh human serum | 3 |
| 500 micrograms/ml HAG in heat inactivated serum (56° C. for 30 minutes) | 3 |
| 500 micrograms/ml monomeric IgG in fresh serum | 3 |

The results are interpreted in the following manner. Since the control well does not contain anti-C1q, it should remain unagglutinated. Consequently, an observed agglutination in the control invalidates the testing procedures and requires repetition. In the testing wells, it should be noted that an agglutination denotes the absence of detectable levels, i.e., less than 40 nanograms, of C1q and is therefore a negative test for immune complexes. A complete inhibition of agglutination, i.e., an absence of agglutination, denotes the presence of C1q in concentrations greater than or equal to 40 nanograms C1q and is a positive test for immune complexes. Partial agglutinations may be interpreted to indicate low levels of C1q less than 40 nanograms but greater than 20 micrograms and imply that further testing should be performed.

Semiquantitation of circulating immune complexes detected by the C1q agglutination inhibition test may be accomplished by a typical titration procedure whereby the PEG precipitate is serally diluted in a series of tubes and tested for C1q as previously described. As is known in such a procedure, the last tube providing complete inhibition of capillary agglutination is assigned the end point. The relative concentration of circulating immune complex present in the sample, either as C1q or HAG depending upon the test sample, may be calculated by multiplying the dilution factor by the original concentration.

Findings

The above procedures were tested to determine their efficacy for identifying the presence of circulating immune complex in sera from a varied population of patients representing both normal and diseased states. This data has been presented in accompanying Table II. Sera was collected, frozen, stored at −70° C. and thawed just prior to testing. The data was collected over a 29 month period and is a composite of three studies.

TABLE II

FREQUENCY OF IC FOUND IN 536 SERA BY THE C1q AGGLUTINATION-INHIBITION TEST

| Disease | P/N* | #IC Pos (%)** |
|---|---|---|
| Rheumatoid Arthritis | 81/113 | 69 (62) |
| Systemic Lupus Erythematosus | 10/12 | 9 (75) |
| Miscellaneous Rheumatologic | 16/18 | 9 (50) |
| Juvenile Rheumatoid Arthritis | 5/5 | 2 (40) |
| Polymyositis/Dermatomyositis | 3/5 | 5 (100) |
| Psoriatic Arthritis | 4/4 | 2 (50) |
| Osteoarthritis | 29/35 | 2 (6) |
| P.A.N./Systemic Vasculitis | 7/10 | 4 (40) |
| Cryoglobulinemia | 2/3 | 2 (67) |
| Ankylosing Spondylitis | 3/3 | 1 (33) |
| Scleroderma | 2/2 | 2 (100) |
| Reiters' Syndrome | 2/3 | 3 (100) |
| Bacterial Endocarditis | 19/36 | 33 (92) |
| Cancer*** | | |
| Colorectal | 13/13 | 3 (23) |
| Breast | 6/6 | 2 (33) |
| Lung | 3/3 | 3 (100) |
| Hodgkins/Lymphoma | 4/4 | 0 (0) |
| Myeloma | 5/7 | 0 (0) |
| Allergy/Hives/Anaphylaxis | 5/5 | 0 (0) |
| Gout | 2/2 | 0 (0) |
| Sarcoid | 2/5 | 5 (100) |
| Acute Hepatitis-Non B | 14/20 | 16 (80) |
| Chronic Hepatitis | 29/34 | 24 (71) |
| Hepatitis B Carriers | 7/8 | 2 (25) |
| Hepatitis Non-viral | 14/17 | 6 (35) |
| Primary Biliary Cirrhosis | 14/14 | 7 (50) |
| Infectious Diseases - Bacterial | 7/8 | 3 (38) |
| Infectious Diseases - Viral | 4/4 | 4 (100) |
| Normal Sera | 109/149 | 7 (5) |

*P/N = #Patients/#Samples
**Sera Positive for IC
***Preoperative Cancer Specimens Only All the normal donors were asymptomatic and not under a physician's care when the blood sample was taken. Of the 149 normal sera tested, seven (5%) gave positive results. Two of these were from the same individual who was bled at a nine month interval. One serum gave partial inhibition, (weak agglutination) and was considered a negative result. The seven positive samples had titers of 1:1.

The 113 samples from patients with rheumatoid arthritis were obtained from two rheumatology services. Of these, 62% exhibited positive results for circulating immune complexes with titers ranging from 1:1-1:64 (40-2560 nanograms C1q).

As expected, samples from patients having other connected tissue diseases and autoimmune diseases showed significant circulating immune complex frequencies, while diseases such as osteoarthritis showed few circulating immune complexes.

Samples were additionally obtained from patients with diagnosed malignancies of the breast, colon, rectum and lung prior to surgery. All such diagnosis were later confirmed in surgery. Of these, 26% of the patients with colectoral or breast cancer had detectable circulating immune complexes while three patients with lung cancer were positive. It is interesting to note that none of the 11 samples tested from patients with Hodgkin's disease or myeloma were positive for circulating immune complexes. On the other hand, patients with infectious diseases such as hepatitis of both viral and nonviral origin, as well as other bacterial or viral infections on In Vitro Human Clq Activities, J. Immunol. 110:820. This labeled material had a specific activity of 1.31 µCi/µg and was kept either frozen at −70° C. until used or preserved as a lyophilized powder.

The comparison was made with a select series of sera obtained from normal donors as well as from patients having rheumatoid arthritis and cancer. The sera was tested both by the Clq methods of the present invention as well as by the $^{125}$I-Clq binding assay method just described. For comparison, freshly thawed aliquots were used. The results observed are provided in accompanying Table III.

TABLE III

COMPARISON OF THE Clq AGGLUTINATION-INHIBITION TEST AND THE I-Clq BINDING ASSAY WITH 172 SERUM SAMPLES

| | Clq Agglutination-Inhibition Test | | | I-Clq Binding Assay | |
|---|---|---|---|---|---|
| Disease | P/N* | #Pos (%)** | #+ (%)*** | P/N* | #Pos (%) |
| Normal | 51/71 | 0 (0) | 1 (1.4) | 51/72 | 6 (8.3) |
| Rheumatoid Arthritis | 20/82 | 45 (54.9) | 2 (2.4) | 20/81 | 42 (51.9)† |
| Cancer | l/18 | 2 (11.1) | 2 (11.1) | 9/18 | 3 (16.7) |

*P/N = #Patients/#Serum Samples Tested
**#Pos = #Sera Positive for IC
***± = Sera Questionable Positive for IC
† 30 Positive by Both Tests
12 Positive by I Binding Assay Only
15 Positive by Clq Agglutination-Inhibition Test Only had high frequencies of detectable circulating immune complex. Indeed, patients with bacterial endocarditis showed an unusually high frequency of detection. Patients having gout and allergic manifestations were, however, negative for circulating immune complexes.

Clearly then, the detection of circulating immune complexes by the above methodologies provides useful data for the clinician as well as important information for the formulation and confirmation of diagnosis.

Comparison with $^{125}$I-Clq binding assay

The Clq methodology of the present invention was compared against a conventional $^{125}$I-Clq binding assay such as that reported by Gabriel et al., Detection of Immune Complexes—The Use of Radioimmunoassays With Clq and Monoclonal Rheumatoid Factor, J. Clin. Invest., 59:990, 1977.

Gabriel's procedure was employed with few modifications: 50 microliters of serum were added to 100 microliters of a 0.2 M EDTA solution at pH 7.5 and incubated at 37° C. for 30 minutes in order to convert endogenous Cl to Clq. To this were added 50 microliters of $^{125}$I-Clq and 1 ml of a 3% PEG 6000 solution to bring the final mixture to 2.5% PEG 6000. Following an incubation period of 1 hour at 5° C. the resulting precipitates were recovered by centrifugation at 1500 g for 20 minutes at 4° C. The supernatants were discarded and the radioactivity of the precipitates measured. The results were recorded as %-Clq bound (precipitated) as compared to a control precipitate obtained from 100 microliter serum, 50 microliters $^{125}$I-Clq and 1 ml 50% trichloracetic acid treated in a manner identical to that above.

The circulating immune complex positive control was prepared by addition of heat aggregated human IgG to fresh serum. Normal human serum was used for the negative controls.

The Clq was isolated from fresh human serum by the methods described previously and labeled using lactoperoxidase as described by the methods of Heusser et al., Effect of Chemical and Enzymatic Radio Iodination Employing the Clq agglutination inhibition test of the present invention, all 71 normal sera tested were negative for circulating immune complex, however, it was noted that one gave partial inhibition indicated by weak agglutination. By the $^{125}$I-Clq binding assay, 8% of these same sera were identified as positive for circulating immune complex. Included in this 8% category was the sample showing weak agglutination by the process of the invention.

When samples from patients having rheumatoid arthritis were tested, 51.9% were positive by the $^{125}$I-Clq binding assay method while 54.9% were positive by the agglutination method of the present invention. In both assays, 30 samples were positive for circulating immune complex. The results obtained using the process of the present invention on samples from patients having rheumatoid arthritis were identical to those found on initial testing (Table II).

With respect to those patients having cancer, two samples were positive by both tests, however, the $^{125}$I-Clq assay indicated an additional sera that was positive for circulating immune complex. One of these three samples, positive by the $^{125}$I-Clq binding assay method was identified as having partial inhibition by the agglutination method of the present invention.

It is noted that circulating immune complex levels following surgery were often reduced or undetectable in many instances however, due to the small number of samples available, statistically significant results could not be identified.

Although the reported experience with the $^{125}$I-Clq binding assay has shown that 8% of normal samples are reactive for circulating immune complex as compared to 0% for the agglutination inhibition test of the present invention, it is hypothesized that such a difference may reflect differences in the methodology employing endogenously bound Clq, such as that by the present invention, and exogenously introduced Clq as employed by the $^{125}$I-Clq binding assay. Further, the exogenously introduced Clq may be dependent on the equilibrium of the $^{125}$I-Clq added with the patient's own naturally occurring Clq which had already become attached to circulating immune complex, if such a complex was present. As noted previously, there is still much to be explained regarding circulating immune complexes and consequently, applicant does not wish to be bound by any theoretical dispositions.

It has been further hypothesized by applicant, that the sera found positive among the normal population of patients tested, represent low levels of humoral immune complexes occurring as a passing event and therefore simply mark the functioning of the immune clearance mechanism. Although the frequency of circulating immune complex containing Clq within the various disease populations studied appears to be representative of data commonly published, it is believed that the low frequency of circulating immune complex among those patients having cancer may be a result of the small sampling size. Those diseases not suspected of being associated with circulating immune complex, for example osteoarthritis, gout, allergy, etc., were negative for circulating immune complexes as expected.

Although the principles of the present invention have been illustrated by the foregoing disclosure, preferred procedures and examples, the invention is not to be construed as being limited to the exact procedure employed herein as it will be apparent to one skilled in the art that various modifications and embodiments of this invention can be made made without departing from the spirit and the scope thereof.

What is claimed is:

1. A method for detecting immune complexes containing endogenously bound Clq in a biological fluid sample comprising the steps of:
    (a) providing Clq coated reagent cells;
    (b) further providing non-human anti-Clq immunoglobulin;
    (c) isolating from the biological fluid sample immune complexes if present in said fluid;
    (d) combining said cells of (a), said immunoglobulin of (b) and the isolate of (c) to form a mixture;
    (e) filling capillary tubes with said mixture of (d);
    (f) allowing any immunological reactions to occur; and
    (g) reading the capillary tube for the presence or absence of agglutination for determining the absence or presence of said immune complexes, respectively.

2. The method as provided in claim 1 wherein the immunoglobulin of step (b) is obtained from a Clq immunized rabbit and the step of isolating the immune complexes includes precipitating with an effective amount of polyethylene glycol.

3. The method as provided in claim 2 wherein step (f) includes incubation for sufficient time at approximately room temperature for the immunological reactions to occur.

4. The method as provided in claim 3 wherein the reagent cells are red blood cells.

5. The method as provided in claim 1 or 3 wherein the filling step further comprises
    (a) sealing one end of the capillary tube; and
    (b) reclining said tube, with said sealed end placed downwardly against a lighted surface disposed at an angle substantially 60° from a generally horizontal plane.

6. The method as provided in claim 4 wherein the red blood cells are human red blood cells.

7. The method as provided in claim 4 wherein the red blood cells are GPO reagent cells.

* * * * *